(12) United States Patent
Chuang et al.

(10) Patent No.: US 9,084,742 B2
(45) Date of Patent: Jul. 21, 2015

(54) COMBINATIONS COMPRISING 3-PHENYLSULFONYL-8-PIPERAZINYL-1YL-QUINOLINE

(75) Inventors: Tsu Tshen Chuang, Harlow (GB); Ann Jacqueline Hunter, Stevenage (GB); David John Virley, Harlow (GB)

(73) Assignee: Axovant Sciences Ltd., Hamilton (BM)

( * ) Notice: Subject to any disclaimer, the term of this patent is extended or adjusted under 35 U.S.C. 154(b) by 612 days.

(21) Appl. No.: 12/746,968

(22) PCT Filed: Dec. 10, 2008

(86) PCT No.: PCT/EP2008/067225
§ 371 (c)(1),
(2), (4) Date: Jun. 9, 2010

(87) PCT Pub. No.: WO2009/074607
PCT Pub. Date: Jun. 18, 2009

(65) Prior Publication Data
US 2010/0267691 A1    Oct. 21, 2010

(30) Foreign Application Priority Data

Dec. 12, 2007 (GB) .................................. 0724281.1
Dec. 12, 2007 (GB) .................................. 0724285.2

(51) Int. Cl.
| | |
|---|---|
| *A61K 31/497* | (2006.01) |
| *A61K 45/06* | (2006.01) |
| *A61K 31/00* | (2006.01) |
| *A61K 31/5513* | (2006.01) |

(52) U.S. Cl.
CPC ............. *A61K 31/00* (2013.01); *A61K 31/5513* (2013.01)

(58) Field of Classification Search
CPC .................................................... A61K 31/497
See application file for complete search history.

(56) References Cited

U.S. PATENT DOCUMENTS

| | | | |
|---|---|---|---|
| 2002/0115670 A1 | 8/2002 | Kelly et al. | |
| 2006/0035888 A1 | 2/2006 | Jonas et al. | |
| 2007/0167431 A1* | 7/2007 | Comery et al. | 514/214.01 |

FOREIGN PATENT DOCUMENTS

| | | |
|---|---|---|
| WO | WO 02/078693 A2 | 10/2002 |
| WO | WO 03080580 A2 * | 10/2003 |
| WO | WO 2004/074243 A2 | 9/2004 |
| WO | WO 2005/040124 A | 5/2005 |
| WO | WO 2007/147883 A | 12/2007 |
| WO | WO 2007/147883 A1 | 12/2007 |

OTHER PUBLICATIONS

Liang et al. Chinese Journal of Psychiatry, 1999, vol. 04, abstract only.*
Geldmacher, D.S. Expert Rev. Neurotherapeutics, 2004, vol. 4, No. 1, pp. 5-16.*
Upton, et al. "5-HT6 receptor antagonists as novel cognitive enhancing agents for Alzheimer's Disease". *Neurotherapeutics*, 5(3): 458-469 (2008).
http://www.gsk-clinicalstudyregister.com/result_comp_list.jsp?compound=SB742457&studyType=All&phase=All&population=All&marketing=All. Sep. 21, 2011.
Foley, et al. Neuropsychopharmacology, 29: 93-100 (2004).
Woolley, et al. Current Drug Targets—CNS & Neurological Disorders, 3: 59-79 (2004).
Ibach, et al. Current Pharmaceutical Design, 10: 231-251 (2004).
Garcia-Alloza, et al. Neuropsychopharmacology, 29: 410-416 (2004).
Woolley, et al. Psychopharmacology, 170: 358-367 (2003).

(Continued)

*Primary Examiner* — Samira Jean-Louis
(74) *Attorney, Agent, or Firm* — Pepper Hamilton LLP

(57) ABSTRACT

The combination of 3-phenylsulfonyl-8-piperazinyl-1yl-quinoline or a pharmaceutically acceptable salt thereof with a second therapeutic agent, wherein the second therapeutic agent is selected from:

(a) a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies;

(b) an antidepressant such as a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant);

(c) an atypical antipsychotic, for example olanzapine, clozapine, prisperidone, quentiapine, aripriprazole or paliperiden; or (d) a therapeutic agent suitable for use in Attention Deficit Disorders/Hyperactivity Syndrome, e.g. methylphenidate (Ritalin) or dexamfetamine (Dexedrine), and also the use of 3-phenylsulfonyl-8-piperazinyl-1yl-quinoline or a pharmaceutically acceptable salt thereof for the treatment of:

a) psychiatric disorders with prominent cognitive deficits e.g. chronic PTSD (Post traumatic stress disorder);

b) non-degenerative disorders with prominent cognitive deficits e.g. MS (multiple Sclerosis), post-chemotherapy, post-CABG (Coronary artery bypass graft), post-stroke; and/or c) paediatric disorders e.g. autism, mental retardation and learning disabilities.

3 Claims, No Drawings

(56) References Cited

OTHER PUBLICATIONS

Riemer, et al. Brief Articles, J. Med. Chem. 46: 1273-1276 (2003).
Woolley, et al. Neuropharmacology, 41:210-219 (2001).
Rogers, et al. Psychopharmacology, 158: 114-119 (2001).
Branchek, et al. Annu. Rev. Pharmacol. Toxicol., 40: 319-334 (2000).
Isaac, et al. Bioorganic & Med. Chem. Letters, 10:1719-1721 (2000).
Bourson, et al. The Journal of Pharmacology & Experimental Therapeutics, 274(1): 173-180 (1995).
Anonymous: "Drug 'treats severe Alzheimer's'". http://newsvote.bbc.co.uk/mpapps/pagetools/print/news.bbc.co.uk/2/hi/health/4832574.stm. Mar. 23, 2006.
Carlos Rojas-Fernandez. Annals of Pharmacotherapy, 35(2): 202-205 (2001).
Birks, et al. The Cochrane Library. http://onlinelibrary.wiley.com/store/10.1002/14651858.CD001190.pub2/asset/CD001190.pdf?v=1&t=h5uxf9xk&s=991bffcda40d23d5edf561ab6543198f531af16d [retrieved on Aug. 14, 2012].
Nordberg, et al. Drug Safety, 19(6): 465-480 (1998).
Roth, et al. Psychopharmacology, 174: 17-24 (2004).
Mitchell, et al. Pharmacology & Therapeutics, 108(3): 320-333 (2005).
Shua-Haim, et al. Neurobiology & Aging, S205: P1-377 (2004).
Davies, et al. Drugs of the Future, 30(5): 479-495 (2005).
S. Totterdell. International Journal of Neuropsychopharmacology, 7: S14 SP.11.01 (2004).
Callahan, et al. 34th Annual Scientific Meeting of the Soc. for Neurosci., San Diego. Oct. 2004.
Johnson, et al. Current Opinion in Drug Discovery and Development, 11 (5): 642-654 (2008).
Lieben, et al. Neuropsychopharmacology, 30: 2169-2179 (2005).
Helm, et al. Neuropharmacology, 48: 956-964 (2005).

\* cited by examiner

COMBINATIONS COMPRISING 3-PHENYLSULFONYL-8-PIPERAZINYL-1YL-QUINOLINE

This application is a 371 of International Application No. PCT/EP2008/067225, filed 10 Dec. 2008, which claims the priority of GB Application Nos. 072428.1, filed 12 Dec. 2007, and 0724285.2, filed 12 Dec. 2007, which are incorporated herein in their entireties.

The present application relates to new uses of $5\text{-HT}_6$ receptor antagonists, specifically 3-phenylsulfonyl-8-piperazinyl-1yl-quinoline, and to the combination of $5\text{-HT}_6$ receptor antagonists, specifically 3-phenylsulfonyl-8-piperazinyl-1yl-quinoline, with a second therapeutic agent.

WO03/080580 discloses compounds of formula (I) and pharmaceutically acceptable salts thereof:

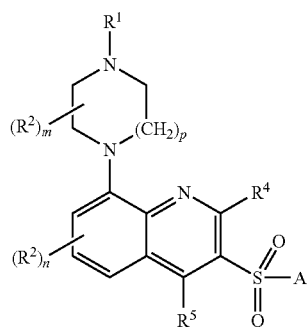

(I)

wherein:
$R^1$ and $R^2$ independently represent hydrogen or $C_{1-6}$ alkyl or $R^1$ is linked to $R^2$ to form a group $(CH_2)_2$, $(CH_2)_3$ or $(CH_2)_4$;
$R^3$, $R^4$ and $R^5$ independently represent hydrogen, halogen, cyano, —$CF_3$, —$CF_3O$, $C_{1-6}$ alkyl, $C_{1-6}$ alkoxy, $C_{1-6}$ alkanoyl or a group —$CONR^6R^7$;
$R^6$ and $R^7$ independently represent hydrogen or $C_{1-6}$ alkyl or together may be fused to form a 5- to 7-membered aromatic or non-aromatic heterocyclic ring optionally interrupted by an O or S atom;
m represents an integer from 1 to 4, such that when m is an integer greater than 1, two $R^2$ groups may instead be linked to form a group $CH_2$, $(CH_2)_2$ or $(CH_2)_3$;
n represents an integer from 1 to 3;
p represents 1 or 2;
A represents a group —$Ar^1$ or —$Ar^2Ar^3$;
$Ar^1$, $Ar^2$ and $Ar^a$ independently represent an aryl group or a heteroaryl group, both of which may be optionally substituted by one or more (eg. 1, 2 or 3) substituents which may be the same or different, and which are selected from the group consisting of halogen, hydroxy, cyano, nitro, trifluoromethyl, trifluoromethoxy, $C_{1-6}$ alkyl, trifluoromethanesulfonyloxy, pentafluoroethyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, arylsulfonyl, arylsulfonyloxy, arylsulfonyl$C_{1-6}$ alkyl, $C_{1-6}$ alkylsulfonamido, $C_{1-6}$ alkylamido, $C_{1-6}$ alkylsulfonamido$C_{1-6}$ alkyl, $C_{1-6}$ alkylamido$C_{1-6}$ alkyl, arylsulfonamido, arylcarboxamido, arylsulfonamido$C_{1-6}$ alkyl, arylcarboxamido$C_{1-6}$ alkyl, aroyl, aroyl$C_{1-6}$ alkyl, aryl$C_{1-6}$ alkanoyl, or a group $CONR^8R^9$ or $SO_2NR^8R^9$, wherein $R^8$ and $R^9$ independently represent hydrogen or $C_{1-6}$ alkyl or together may be fused to form a 5- to 7-membered aromatic or non-aromatic heterocyclic ring optionally interrupted by an O or S atom;
or solvates thereof.

Specifically disclosed is 3-phenylsulfonyl-8-piperazinyl-1yl-quinoline (Example 16) and its hydrochloride salt (Example 2).

3-Phenylsulfonyl-8-piperazinyl-1yl-quinoline can be prepared as described in WO03/080580 or by the further process described in WO07/039,238. WO05/040124 discloses a further polymorphic form of 3-phenylsulfonyl-8-piperazinyl-1yl-quinoline as Form III. These International Patent Applications are incorporated herein in their entirety.

Compounds of formula (I) and their pharmaceutically acceptable salts are disclosed in WO03/080580 as having affinity for the $5\text{-HT}_6$ receptor and are believed to be of potential use in the treatment of certain CNS disorders such as anxiety, depression, epilepsy, obsessive compulsive disorders, migraine, cognitive memory disorders (e.g. Alzheimers disease, age related cognitive decline and mild cognitive impairment), Parkinsons Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia (in particular cognitive deficits of schizophrenia), stroke and also disorders associated with spinal trauma and/or head injury such as hydrocephalus. WO03/080580 also discloses that Compounds of formula (I) and their pharmaceutically acceptable salts are expected to be of use in the treatment of certain GI (gastrointestinal) disorders such as IBS (Irritable Bowel Syndrome) and in the treatment of obesity.

It will be appreciated by those skilled in the art that the term cognitive memory disorders includes other neurodegenerative disorders associated with dementia, e.g. VaD (Vascular Dementia), DLB (dementia with Lewy Bodies), Mixed AD+CVD (Alzheimer's Disease and Cardiovascular Disease) and HD (Huntingdon's Disease).

US2007/0167431 and WO07/087,151 (both Wyeth) disclose a method for the treatment of a cognitive disorder such as Alzheimer's disease in a patient in need thereof which comprises providing to said patient a therapeutically effective amount of a combination of an acetylcholinesterase inhibitor and a $5\text{-HT}_6$ receptor antagonist.

US2007/0167431 discloses that the acetylcholinesterase inhibitors suitable for use are donepezil (i.e. Aricept™ manufactured by Pfizer), galanthamine (i.e. Razadyne™, manufactured by Johnson and Johnson), rivastigmine (i.e. Exelon™, manufactured by Novartis) or any other compounds known to inhibit acetylcholinesterase. A number of patent applications were cited therein which disclosed 5-HT6 antagonists suitable for use. Furthermore the following 5HT6 compounds were listed by name, 3-(1-naphthylsulfonyl)-5-piperazin-1yl-1H-indazole, N,N-dimethyl-3-{3-(1-naphthylsulphonyl)-1H-indazol-5-yl]oxy}propan-1-amine, (2-{[3-(1-naphthylsulphonyl)-1H-indazol-7-yl]oxy}ethyl)amine, 1-(phenylsulphonyl)-4-(1-piperazinyl)-1H-indazole, 5-chloro-N-[4-methoxy-3-(1-piperazinyl)phenyl]-3-methyl-benzo(b)thiophene-2-sulfonamide (SB-271046), 4-amino-N-[2,6-bis(methylamino)pyrimidin-4-yl]benzenesulfonamide (Ro 04-6790, 4-amino-N-[2,6-bis(methylamino) pyridin-4-yl]benzenesulfonamide (Ro 63-0563), SB357134, SB399885, GSK-742457, LY4833518/SGS-518, Ro43-68554 and PRX-07034.

The present invention provides the combination of a $5\text{-HT}_6$ receptor antagonist, specifically 3-phenylsulfonyl-8-piperazinyl-1yl-quinoline or a pharmaceutically acceptable salt thereof, with a second therapeutic agent. In one embodiment the present invention provides a combination of 3-phenylsulfonyl-8-piperazinyl-1yl-quinoline or a pharmaceutically acceptable salt thereof with a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies.

Examples of putative metabolic/mitochondrial modulators are Ketasyn™, RSG-XR, intranasal insulin and Dimebon.

Examples of β-amyloid aggregation inhibitors and β-amyloid immunotherapies include PBT2 (Prana Biotechnology), ELND005/AZD-103 (Elan and Transition Therapeutics), Gammagard/IGIV (Baxter International), monoclonal antibody LY2062430 (Eli Lilly), and bapineuzumab (Wyeth/Elan).

Examples of Tau-targeted therapeutics include tetramethylthionine chloride (REMBER™, TauRX) and AL-108 (Allon).

This combination may be useful in the treatment of cognitive memory disorders, for example Alzheimer's disease, age related cognitive decline and mild cognitive impairment, neurodegenerative disorders for example dementia including vascular dementia (VaD), dementia with Lewy Bodies (DLB), Alzheimer's Disease and Cardiovascular Disease (Mixed AD+CVD) and Huntingdon's Disease (HD).

Accordingly the present invention also provides a method for the treatment of cognitive memory disorders, for example Alzheimer's disease, age related cognitive decline and mild cognitive impairment, neurodegenerative disorders for example dementia including vascular dementia (VaD), dementia with Lewy Bodies (DLB), Alzheimer's Disease and Cardiovascular Disease (Mixed AD+CVD) and Huntingdon's Disease (HD) in a patient in need thereof which comprises providing to said patient a therapeutically effective amount of a combination of 3-phenylsulfonyl-8-piperazinyl-1yl-quinoline or a pharmaceutically acceptable salt thereof, with a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies.

One embodiment is directed to combinations of 3-phenylsulfonyl-8-piperazinyl-1yl-quinoline or a pharmaceutically acceptable salt thereof and a second therapeutic agent selected from donepezil, rivastigmine, tetrahydroaminoacridine, memantine, galantamine, 6-[(3-cyclobutyl-2,3,4,5-tetrahydro-1H-3-benzazepin-7-yl)oxy]-N-methyl-3-pyridinecarboxamide hydrochloride or 1-{6-[(3-cyclobutyl-2,3,4,5-tetrahydro-1H-3-benzazepin-7-yl)oxy]-3-pyridinyl}-2-pyrrolidinone.

At a mechanistic level, pharmacodynamic interactions between an acetylcholinesterase inhibitor and a 5HT$_6$ receptor antagonist are feasible. In preclinical studies in rats 3-phenylsulfonyl-8-piperazinyl-1yl-quinoline induces a small increase in the extra cellular levels of acetylcholine in the prefrontal cortex. Although the underlying mechanism is still unknown, it is likely due to increases in the release of acetylcholine from cholinergic neurons, On the other hand, donepezil increases the extracellular levels of acetylcholine by inhibiting the acetylcholinesterase to reduce the degradation of acetylcholine. Therefore this action may prevent the degradation of acetylcholine induced by 3-phenylsulfonyl-8-piperazinyl-1yl-quinoline resulting in a net increased level of acetylcholine that may influence cognitive functions.

In another embodiment the present invention provides a combination of 3-phenylsulfonyl-8-piperazinyl-1yl-quinoline or a pharmaceutically acceptable salt thereof with an antidepressant, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant). Examples of specific antidepressant compounds are described below.

| Medication | Trade name | Group |
| --- | --- | --- |
| Amitriptyline | Tryptizol | Tricyclic |
| Clomipramine | Anafranil | Tricyclic |
| Citalopram | Cipramil | SSRI |
| Dosulepin | Prothiaden | Tricyclic |
| Doxepin | Sinequan | Tricyclic |
| Fluoxetine | Prozac | SSRI |
| Imipramine | Tofranil | Tricyclic |
| Lofepramine | Gamanil | Tricyclic |
| Mirtazapine | Zispin | NaSSA |
| Moclobemide | Manerix | MAOI |
| Nortriptyline | Allegron | Tricyclic |
| Paroxetine | Seroxat | SSRI |
| Phenelzine | Nardil | MAOI |
| Reboxetine | Edronax | SNRI |
| Sertraline | Lustral | SSRI |
| Tranylcypromine | Parnate | MAOI |
| Trazodone | Molipaxin | Tricyclic-related |
| Venlafaxine | Efexor | SNRI |

In a further embodiment the present invention provides a combination of 3-phenylsulfonyl-8-piperazinyl-1yl-quinoline or a pharmaceutically acceptable salt thereof and an atypical antipsychotic, for example olanzapine, clozapine, prisperidone, quentiapine, aripriprazole or palipexiden.

This combination may be useful in the treatment of schizophrenia. Accordingly, in yet another aspect the present invention provides a method for the treatment of schizophrenia in a patient in need thereof which comprises providing to said patient a therapeutically effective amount of a combination of 3-phenylsulfonyl-8-piperazinyl-1yl-quinoline or a pharmaceutically acceptable salt thereof, with an atypical antipsychotic, for example olanzapine, clozapine, prisperidone, quentiapine, aripriprazole or palipexiden.

In a further embodiment the present invention provides a combination of 3-phenylsulfonyl-8-piperazinyl-1yl-quinoline or a pharmaceutically acceptable salt thereof and a second therapeutic agent suitable for use in Attention Deficit Disorders/Hyperactivity Syndrome, e.g. methylphenidate (Ritalin) or dexamfetamine (Dexedrine).

In a further aspect the present invention also provides the use of a combination of 3-phenylsulfonyl-8-piperazinyl-1yl-quinoline or a pharmaceutically acceptable salt thereof and a second therapeutic agent in the manufacture of a medicament for use in the treatment of the above disorders.

Accordingly, in one embodiment the present invention provides the use of a combination of 3-phenylsulfonyl-8-piperazinyl-1yl-quinoline or a pharmaceutically acceptable salt thereof with a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies, in the manufacture of a medicament for use in the treatment of cognitive memory disorders, for example Alzheimer's disease, age related cognitive decline and mild cognitive impairment, neurodegenerative disorders for example dementia including vascular dementia (VaD), dementia with Lewy Bodies (DLB), Alzheimer's Disease and Cardiovascular Disease (Mixed AD+CVD) and Huntingdon's Disease (HD).

In another embodiment the present invention provides the use of a combination of 3-phenylsulfonyl-8-piperazinyl-1yl-quinoline or a pharmaceutically acceptable salt thereof and an atypical antipsychotic, for example olanzapine, clozapine, prisperidone, quentiapine, aripriprazole or paliperiden in the manufacture of a medicament for use in the treatment of schizophrenia.

The present invention is also directed to new uses of 3-phenylsulfonyl-8-piperazinyl-1yl-quinoline or a pharmaceutically acceptable salt thereof; specifically
a) further psychiatric disorders with prominent cognitive deficits e.g. chronic PTSD (Post traumatic stress disorder);
b) non-degenerative disorders with prominent cognitive deficits: MS (multiple Sclerosis), post-chemotherapy, post-CABG (Coronary artery bypass graft), post-stroke; and
c) paediatric disorders: autism, mental retardation and learning disabilities.

The invention further provides a method of treatment or prophylaxis of these disorders, in mammals including humans, which comprises administering to the sufferer a therapeutically effective amount of 3-phenylsulfonyl-8-piperazinyl-1yl-quinoline or a pharmaceutically acceptable salt thereof.

The invention also provides the use of a 3-phenylsulfonyl-8-piperazinyl-1yl-quinoline or a pharmaceutically acceptable salt thereof in the manufacture of a medicament for use in the treatment or prophylaxis of these disorders.

The invention also provides combinations of 3-phenylsulfonyl-8-piperazinyl-1yl-quinoline and a second therapeutic agent for use in these disorders.

In respect of the treatment of PTSD, the second therapeutic agent may be selected from: serotonergic antidepressants (SSRIs), e.g. fluoxetine (Prozac), sertraline (Zoloft), paroxetine (Paxil), trazodone (Desyrel); medicines that help decrease the physical symptoms associated with PTSD, e.g. clonidine (Catapres), guaneficine (Tenex), and propranolol; mood stabilizers such as lamotrigine (Lamictal), tiagabine (Gabitril), divalproex sodium (Depakote); monoamine oxadazine inhibitors, phenelzine (Nardil); antiadrenergic agents, e.g. clonidine (Catapres), propanolol (Inderal) and guanfacine (Tenex), mood stabilizers that are also antipsychotics, like risperidone (Risperdal), olanzapine (Zyprexa), and quetiapine (Seroquel).

In respect of the treatment of MS, the second therapeutic agent may be selected from: steroids, e.g. methylprednisolone (eg Depo-Medrone), prednisone, dexamethasone disease-modifying agents e.g. interferon beta-1a (Avonex or Rebif), interferon beta-1b (Betaferon), glatiramer acetate (Copaxone) injections or mitoxantrone (Novantrone); symptomatic agents e.g. Muscle Relaxants (Baclofen, Dantrolene, Tizanidine, Cyclobenzaprine, Clonazepam, Diazepam); Anticholinergics (Propantheline, Tolterodine Dicyclomine); Urinary Tract Antispasmodics (Oxybutynin); Tricyclic Antidepressants (Amitriptyline, Imipramine); Antidiuretic Hormone (desmopressin and desmopressin acetate); Anticonvulsants (carbamazepine, phenyloin, acetazolamide, lamotrigine); Central Nervous System Stimulants (pemoline); Selective Serotonin Reuptake Inhibitors (SSRIs) (citalopram, fluoxetine, paroxetine, sertraline); Non-Steroidal Anti-Inflammatory Drugs (NSAIDS) (ibuprofen, naproxen, ketoprofen); and Phosphodiesterase-5 Inhibitors (sildenafil, tadalafil, vardenafil).

Additionally the second therapeutic agent for use in the treatment of MS or its associated symptoms may be selected from an H3 receptor antagonist, 6-[(3-cyclobutyl-2,3,4,5-tetrahydro-1H-3-benzazepin-7-yl)oxy]-N-methyl-3-pyridinecarboxamide hydrochloride or 1-{6-[(3-cyclobutyl-2,3,4,5-tetrahydro-1H-3-benzazepin-7-yl)oxy]-3-pyridinyl}-2-pyrrolidinone; S1P1 agonists; anti-CD20 monoclonal antibody therapies such as rituximab, ofatumumab; anti-CD3 monoclonal antibody therapies such as otelixizumab; rosiglitazone (Avandia™), alpha 4 integrin antagonist e.g firategrast, natalizumab (TYSABRI™).

Additionally the second therapeutic agent for use in the treatment of MS or its associated symptoms may be selected from BG12 (Biogen Idec), an S1P agonist e.g. Fingolimod, an immunosuppressant e.g. Laquinimod, Teriflunomide; an estrogen agonist e.g. Trimesta.

In respect of the treatment post chemotherapy, the second therapeutic agent may be selected from: Aldesleukin or IL-2 (Proleukin), Alemtuzumab (MabCampath), Amsacrine (acridinyl anisidide; m-AMSA), Anastrozole (Arimidex), Asparaginase (Crisantaspase), Bevacizumab (Avastin), Bicalutamide (Casodex), Bleomycin, Bortezomib (Velcade), Busulfan, (Campto) Irinotecan, Capecitabine (Xeloda) Carboplatin (Paraplatin), Carmustine (BCNU), Cetuximab, Chlorambucil, Cisplatin, Cladribine (2-CdA, Leustatin), Co-codamol, Cyclophosphamide, Cyproterone acetate (Cyprostat), Cytarabine (Ara C, cytosine arabinoside), Dacarbazine (DTIC), Dactinomycin (Actinomycin D), Daunorubicin, Disodium pamidronate (Aredia), Docetaxel (Taxotere), Doxorubicin, Epirubicin, Erlotinib (Tarceva), Estramustine (Emcyt, Estracyte), Etoposide (VP16, Etopophos), Exemestane (Aromasin), Fentanyl (Durogesic), Fludarabine, Fluorouracil (5FU), Flutamide (Drogenil), Gemcitabine (Gemzar), (Herceptin) Trastuzumab, Goserelin (Zoladex) for breast cancer, Goserelin (Zoladex) for prostate cancer, Hydroxycarbamide (used to be called hydroxyurea), Ibandronic acid (Bondronat), Ibritumomab (Zevalin), Ibuprofen, Idarubicin (Zavedos) Ifosfamide, Imatinib (Glivec), Interferon (Roferon, Intron A), Irinotecan (Campto), Interleukin, Lapatinib (Tykerb), Letrozole (Femara), Liposomal Doxorubicin (Caelyx, Myocet, Doxcil), Lomustine (CCNU), Melphalan, Mercaptopurine (6-MP, Purinethol), Methotrexate, Mitomycin C, Mitoxantrone, Morphine, Oxaliplatin, Paclitaxel (Taxol), Pentostatin, Procarbazine, Raltitrexed (Tomudex), Rituximab (Mabthera), Sodium clodronate (Bonefos, Loron), Streptozocin (Zanosar), Steroids, Tamoxifen, (Taxol) Paclitaxel, (Taxotere) Docetaxel, Tegafur with uracil (Uftoral), Temozolomide (Temodal), Tioguanine (Lanvis, 6-TG, 6-tioguanine, Tabloid), Thiotepa (Thioplex, Triethylenethiophosphoramide), (Tomudex) Raltitrexed, Topotecan (Hycamtin), Tretinoin (Vesanoid, ATRA), Treosulfan, Vinblastine (Velban), Vincristine (Oncovin) Vindesine (Eldisine), Vinorelbine (Navelbine), Zevalin (90Y Ibritumomab tiuxetan) and Zoledronic acid (Zometa).

Specifically the second therapeutic agent may be lapatinib, which may also be used in conjunction with capecitabine.

In respect of treatment after a stroke, the second therapeutic agent may be selected from alteplase (Actilyse), aspirin, dipyridamole, fluvastatin sodium (Lescol), clopidogrel hydrogen sulphate (Plavix), ramipril (Tritace) and simvastatin (Simvador, Zocor).

It will be appreciated that reference to treatment is intended to include prophylaxis as well as the alleviation of established symptoms.

The two therapeutic agents may be administered simultaneously or sequentially and, when administration is sequential, either may be administered first. When administration is simultaneous, the combination may be administered either in the same or different pharmaceutical composition.

The two therapeutic agents may be used either as separate formulations or as a single combined formulation. When combined in the same formulation it will be appreciated that the two compounds must be stable and compatible with each other and the other components of the formulation.

Therefore, in further aspect the present invention also provides pharmaceutical compositions comprising an effective amount of a combination of a 5-HT$_6$ receptor antagonist, specifically 3-phenylsulfonyl-8-piperazinyl-1yl-quinoline or a pharmaceutically acceptable salt thereof and a second therapeutic agent, and a pharmaceutically acceptable carrier.

In one embodiment the second therapeutic agent is an agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists GABA-ergic antagonists, H3 antagonists or disease modifying agents such as β or γ-secretase inhibitors.

In another embodiment the second therapeutic agent is an antidepressant, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant).

In another embodiment the second therapeutic agent is an atypical antipsychotic, for example olanzapine, clozapine, prisperidone, quentiapine, aripriprazole or palipiderin.

In another embodiment the second therapeutic agent is a therapeutic agent suitable for use in Attention Deficit Disorders/Hyperactivity Syndrome, e.g. methylphenidate (Ritalin) or dexamfetamine (Dexedrine).

When formulated separately they may be provided in any convenient formulation, conveniently in such manner as are known for such compounds in the art.

A pharmaceutical composition may be prepared by admixture, suitably at ambient temperature and atmospheric pressure, and is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use.

Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

Compositions may, if desired, be presented in a pack or dispenser device which may contain one or more unit dosage forms containing the active ingredients. The pack may, for example, comprise metal or plastic foil, such as a blister pack. Where the compounds are intended for administration as two separate compositions these may be presented, for example, in the form of a twin pack.

Pharmaceutical compositions may also be prescribed to the patient in "patient packs" containing the whole course of treatment in a single package, usually a blister pack. Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination by means of a single patient pack, or patient packs of each composition, including a package insert directing the patient to the correct use of the combination is a desirable additional embodiment.

According to a further embodiment there is provided a patient pack comprising at least one active ingredient, of the combination and an information insert containing directions on the use of the combination.

According to another embodiment there is provided a double pack comprising in association for separate administration of 3-phenylsulfonyl-8-piperazinyl-1yl-quinoline and the second therapeutic agent.

The dose of 3-phenylsulfonyl-8-piperazinyl-1yl-quinoline used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

The dose of 3-phenylsulfonyl-8-piperazinyl-1yl-quinoline used in combination with a second therapeutic agent may be same as when it is used on its own or may be different. It may be possible that the dose of either drug used may be lower when used in combination than when used separately.

Suitable behavioural models of cognition known to the person of ordinary skill in the art, for example object recognition memory in young Sprague-Dawley and aged Fisher rats, Water Maze model to investigate spatial learning and memory in young and aged Fisher rats.

A suitable animal model for studying therapeutic drugs against post-traumatic stress disorder is described by Aharon Levy, in Military Medicine, December 2001.

A suitable animal model for studing multiple sclerosis is the experimental autoimmunal encephalomyelitis (EAE) model.

Patient Study for Schizophrenia

The study may be performed as a multicenter, double-blind, placebo controlled randomised, parallel group determination of efficacy of 3-phenylsulfonyl-8-piperazinyl-1yl-quinoline in combination with an atypical antipsychotic agent approved for the treatment of schizophrenia vs an atypical antipsychotic agent approved for the treatment of schizophrenia with placebo.

For example, the study may be performed using a therapeutic dose within the prescribed guidelines of Risperidone.

The patients may receive an appropriate dose of the atypical antipsychotic agent (defined antipsychotic agent or antipsychotic), and, depending on which group they belonged, a therapeutically effective amount 3-phenylsulfonyl-8-piperazinyl-1yl-quinoline once daily or placebo over 12 weeks after a brief wash-out period of earlier antipsychotic medication.

During the wash-out period, a benzodiazepine preparation (mostly lorazepam) may be prescribed, if necessary. Patients with agitation, anxiety, or sleeping problems may be also medicated with lorazepam during the study.

Efficacy and tolerability of 3-phenylsulfonyl-8-piperazinyl-1yl-quinoline/antipsychotic agent vs placebo/antipsychotic agent will be assessed using the following endpoints—positive and negative syndrome scale (PANSS), Clinical Global Impression score (CGI), AIMS, Simpson and Angus, Barnes Akathisia, Calgary Depression Scale and cognition endpoints.

The use of biperiden may be monitored as a possible indicator for side effects of the antipsychotic medication.

In order to exclude the chance that possible differences in the therapeutic effectiveness between the two groups might be due to non-compliance during the antipsychotic therapy or to differences in the antipsychotic agent metabolism, the plasma levels of this drug may be monitored during the study.

The statistics may be performed according to the criterion of "last observation carried forward" (LOCF), i.e., the last PANSS scores of the patients who dropped out before the end of the study were carried forward to all subsequent observation days.

For the comparison of the main efficacy parameter, the mean change in the PANSS between the two treatment groups, t-tests for independent samples may be employed. With reference to the underlying hypothesis of a better outcome of 3-phenylsulfonyl-8-piperazinyl-1yl-quinoline/antipsychotic agent group, a significance of $p<0.05$ may be calculated in the one-tailed t-test and used as the basis for the estimation of the sample size (statistical power) and for the comparison of the groups. For all other comparisons, two-tailed t-tests may be used.

The improved effectiveness of the combination therapy with 3-phenylsulfonyl-8-piperazinyl-1yl-quinoline/antipsychotic agent in comparison to antipsychotic monotherapy may be clearly shown by the significantly lower PANSS global scores after the $2^{nd}$ to 12 weeks of treatment.

Therefore, it could be excluded that the observed differences in the therapeutic effectiveness between the two groups may be due to incompatibility during the antipsychotic agent therapy or differences in antipsychotic metabolism.

The combination of 3-phenylsulfonyl-8-piperazinyl-1yl-quinoline and an atypical antipsychotic agent according to the present invention thus may show improved results compared to the monopreparation of the atypical antipsychotic agent with regard to effectiveness in the treatment of schizophrenia.

Depression/Anxiety Study

Activity of 3-phenylsulfonyl-8-piperazinyl-1yl-quinoline in combination with SSRI inhibitors, vs. depression/anxiety may be evaluated according to the following models:

Porsolt test in mouse for SSRI/TCA (tricyclic antidepressants) (Porsolt et al 1977, Arch Int Pharmacodyn Ther,: 229, 327-336);

Chronic mild stress in rat for SSRI/TCA (Willner, 1991, TiPS,: 12, 131-136);

Maternal deprivation in rat pups for SSRI (or modulator of serotonin receptors)/TCA (Gardner, 1985, J. Pharmacol. Methods 14: 181-187);

Rat social interaction after chronic treatment with SSRI/TCA (File, 1980 J. Neurosci Methods, 2:219-238; Lightowler et al., 1994, Pharmacol., Biochem. Behaviour,: 49, 281-285);

Gerbil social interaction after chronic treatment with SSRI (or modulator of serotonin receptors)/TCA (File, 1997, Pharmacol. Biochem. Behav. 58: 747-752).

Clinical Trials

The usefulness of the compound for treating a Depressive Disorder can be supported by the following studies as described.

Clinical Observations

A double-blind multicenter clinical trial may be designed to assess the safety and efficacy of 3-phenylsulfonyl-8-piperazinyl-1yl-quinoline of the present invention in combination with an SSRI such as paroxetine for treatment of Bipolar Disorder, Bipolar Depression or Unipolar Depression. Patients are randomized to 3-phenylsulfonyl-8-piperazinyl-1yl-quinoline, an SSRI such as paroxetine or 3-phenylsulfonyl-8-piperazinyl-1yl-quinoline plus an SSRI.

In one such study, an 8-week, double blind trial, 28 patients diagnosed with treatment-resistant major depression would be randomized to one of three treatment arms: (1) paroxetine and placebo; (2) 3-phenylsulfonyl-8-piperazinyl-1yl-quinoline and placebo; or (3) paroxetine plus 3-phenylsulfonyl-8-piperazinyl-1yl-quinoline. The efficacy of the treatment may be monitored using the HAMD-21 (Hamilton M. *Journal of Neurology, Neurosurgery & Psychiatry.* 1960.23: 56-62, and Hamilton M. *Development of a rating scale for primary depressive illness*. British Journal of Social and Clinical Psychology. 1967; 6:278-296), Montgomery-Asberg Depression Rating Scale (MADRS) (Montgomery S A, Asberg M. *A new depression scale designed to be sensitive to change*. British Journal of Psychiatry. 1979; 134:382-389), and the Clinical Global Impression (CGI)-Severity of Depression rating scale (Guy, W. ECDEU Assessment Manual for Psychopharmacology. Revised ed. US Dept of Health, Education and Welfare, Bethesda, Md. 1976).

All publications, including but not limited to patents and patent applications, cited in this specification are herein incorporated by reference as if each individual publication were specifically and individually indicated to be incorporated by reference herein as though fully set forth.

The invention claimed is:

1. A method for the treatment of a cognitive memory disorder in a patient in need thereof, said method comprising providing to said patient a therapeutically effective amount of 3-phenylsulfonyl-8-piperazinyl-1-yl-quinoline or a pharmaceutically acceptable salt thereof, and donepezil,
   wherein said cognitive memory disorder is selected from the group consisting of vascular dementia, dementia with Lewy Bodies, and dementia associated with Huntingdon's Disease,
   and wherein 20 to 40 mg of 3-phenylsulfonyl-8-piperazinyl-1yl-quinoline, or a pharmaceutically acceptable salt thereof, is provided to said patient.

2. The method according to claim 1, wherein the cognitive memory disorder is dementia with Lewy Bodies.

3. A method for improving the cognitive function of a patient suffering from dementia with Lewy Bodies, said method comprising administering to said patient 20 to 40 mg of 3-phenylsulfonyl-8-piperazinyl-1-yl-quinoline or a pharmaceutically acceptable salt thereof, and donepezil.

* * * * *